United States Patent [19]

Hutt et al.

[11] Patent Number: 4,571,396

[45] Date of Patent: Feb. 18, 1986

[54] ANTIBACTERIAL AGENTS

[75] Inventors: Marland P. Hutt, Saline; Thomas F. Mich; Townley P. Culbertson, both of Ann Arbor, all of Mich.

[73] Assignee: Warner-Lambert Company, Morris Plains, N.J.

[21] Appl. No.: 708,565

[22] Filed: Mar. 11, 1985

Related U.S. Application Data

[63] Continuation-in-part of Ser. No. 600,934, Apr. 16, 1984, abandoned.

[51] Int. Cl.[4] .................. A61K 31/47; A61K 31/495; C07D 471/04; C07D 471/08
[52] U.S. Cl. ..................................... 514/249; 514/222; 514/233; 514/236; 514/300; 514/304; 514/312; 544/32; 544/101; 544/344; 544/349; 546/94; 546/123; 546/126; 546/156
[58] Field of Search ................. 544/32, 101, 344, 349; 546/94, 123, 126, 156; 514/222, 233, 236, 249, 300, 304, 312

[56] References Cited

U.S. PATENT DOCUMENTS

| | | | |
|---|---|---|---|
| 3,753,993 | 8/1973 | Lesher et al. | 546/156 |
| 3,907,808 | 9/1975 | Lesher et al. | 546/156 |
| 4,146,719 | 3/1979 | Irikura | 544/363 |
| 4,292,317 | 9/1981 | Pesson | 546/156 X |
| 4,341,784 | 7/1982 | Matsumoto et al. | 546/123 |
| 4,382,892 | 5/1983 | Hayakawa et al. | 544/101 |
| 4,399,134 | 5/1983 | Ishikawa et al. | 546/156 X |
| 4,448,962 | 5/1984 | Ishikawa et al. | 546/156 X |

FOREIGN PATENT DOCUMENTS

| | | |
|---|---|---|
| 47005 | 3/1982 | European Pat. Off. . |
| 106489 | 4/1984 | European Pat. Off. . |
| 149286 | 9/1982 | Japan . |
| 203085 | 12/1982 | Japan . |
| 72589 | 4/1983 | Japan . |
| 109181 | 12/1983 | Japan . |

OTHER PUBLICATIONS

Koga et al., J. Med. Chem., 23, (1980), pp. 1358-1363.
Rufer et al., Eur. J. Med. Chem.-Chimica Therapeutica, 29, (1977), pp. 27-29.

Primary Examiner—Richard L. Raymond
Attorney, Agent, or Firm—Ronald A. Daignault

[57] ABSTRACT

Novel naphthyridine-, quinoline- and benzoxazine-carboxylic acids as antibacterial agents are described as well as methods for their manufacture, formulation, and use in treating bacterial infections including the description of certain novel intermediates used in the manufacture of the antibacterial agents.

32 Claims, No Drawings

ANTIBACTERIAL AGENTS

CROSS-REFERENCE TO RELATED APPLICATION

This is a continuation-in-part of U.S. Ser. No. 600,934, filed Apr. 16, 1984, and now abandoned.

BACKGROUND OF THE INVENTION

U.S. Pat. No. 4,341,784 discloses certain substituted 7-(3-amino-1-pyrrolidinyl)-1-ethyl-6-fluoro-1,4-dihydro-4-oxo-1,8-naphthyridine-3-carboxylic acids having the general formula:

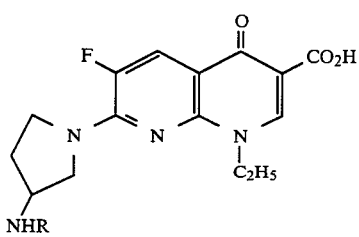

The compounds are disclosed to have antibacterial activity.

The Journal of Medicinal Chemistry, 23, 1358 (1980) discloses certain substituted quinoline-3-carboxylic acids having the structural formula:

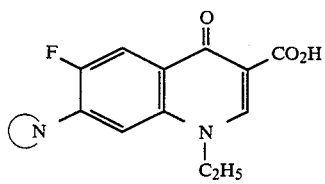

wherein

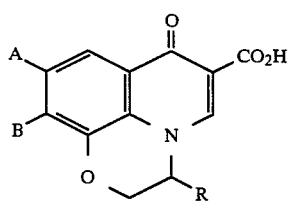

may be pyrrolidinyl. See also U.S. Pat. No. 4,146,719. The compounds are disclosed to have antibacterial activity.

European patent application No. 81 10 6747, Publication No. 047,005, published Mar. 10, 1982, discloses certain benzoxazine derivatives having the structural formula:

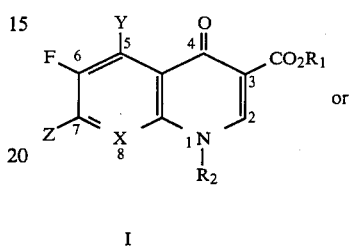

wherein A is halogen and B may be a cyclic amine substituent such as pyrrolidine, or piperidine.

Certain 7-heterocyclic substituted 1,8-naphthyridines are disclosed in Eur. J. Med. Chem.-Chimica Therapecutica, 29, 27 (1977). U.S. Pat. Nos. 3,753,993 and 3,907,808 disclose certain 7-pyridylquinolines.

Japanese Patent Publication No. 109,181, published Dec. 27, 1983, described pyrido (1,2,3-de) (1,4)benzoxaxine-6-carboxylic acid derivatives.

The references teach that these compounds possess antibacterial activity.

SUMMARY OF THE INVENTION

The invention in a first generic chemical compound aspect is a compound having the structural formula I or Ia.

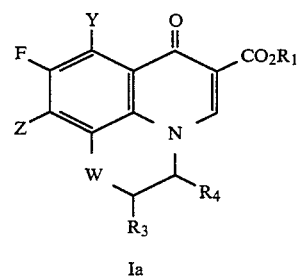

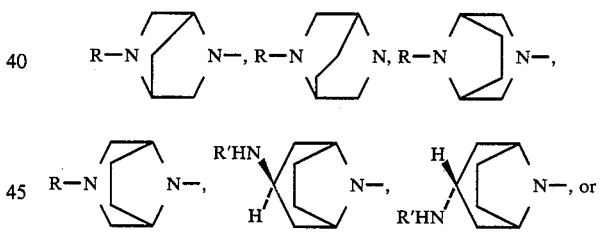

wherein Z is

in which R is hydrogen, alkyl of one to three carbon atoms, hydroxyalkyl of two or three carbon atoms, benzyl or p-aminobenzyl; $R^1$ is hydrogen or alkanoyl of from one to three carbon atoms; X is CH, CF, or N; Y is hydrogen, fluoro, or amino; W is O, NR, S or CH, $R_1$ is hydrogen, alkyl having from one to six carbon atoms or a cation; $R_2$ is alkyl having from one to four carbon atoms, vinyl, haloalkyl, or hydroxyalkyl having from two to four carbon atoms, or cycloalkyl having three to six carbon atoms; $R_3$ is hydrogen or alkyl having from one to three carbon atoms; $R_4$ is hydrogen or alkyl from one to three carbon atoms, and the pharmaceutically acceptable acid addition or base salts thereof.

Preferred compounds of this invention are those wherein Y is hydrogen.

Preferred compounds of this invention are also those of formula I wherein X is N, or C—F.

Other preferred compounds of this invention are those of formula Ia wherein and $R_3$ and $R_4$ are each hydrogen or methyl.

Other preferred compounds of this invention are those wherein $R_1$ is hydrogen or a pharmaceutically acceptable base salt such as a metal or amine salt.

Other preferred compounds of this invention are those wherein $R_2$ is ethyl, vinyl, 2-fluoroethyl or cyclopropyl.

Particularly preferred species of the invention are the compounds having the names:

7-(2,5-diazabicyclo[2.2.2]oct-2-yl)-1-ethyl-6,8-difluoro-1,4-dihydro-4-oxo-3-quinolinecarboxylic acid;

7-(2,5-diazabicyclo[2.2.2]oct-2-yl)-1-ethyl-6-fluoro-1,4-dihydro-4-oxo-1,8-naphthyridine-3-carboxylic acid;

7-(2,5-diazabicyclo[2.2.2]oct-2-yl)-1-cyclopropyl-6,8-difluoro-1,4-dihydro-4-oxo-3-quinolinecarboxylic acid;

7-(2,5-diazabicyclo[2.2.2]oct-2-yl)-1-cyclopropyl-6-fluoro-1,4-dihydro-4-oxo-1,8-naphthyridine-3-carboxylic acid;

7-[3-(exo-amino)-8-azabicyclo[3.2.1]oct-8-yl]-1-ethyl-6,8-difluoro-1,4-dihydro-4-oxo-3-quinolinecarboxylic acid;

7-[3-(exo-amino)-8-azabicyclo[3.2.1]oct-8-yl]-1-ethyl-6-fluoro-1,4-dihydro-4-oxo-1,8-naphthyridine-3-carboxylic acid;

7-[3-(exo-amino)-8-azabicyclo[3.2.1]oct-8-yl]-1-cyclopropyl-6,8-difluoro-1,4-dihydro-4-oxo-3-quinolinecarboxylic acid;

7-[3-(exo-amino)-8-azabicyclo[3.2.1]oct-8-yl]-1-cyclopropyl-6-fluoro-1,4-dihydro-4-oxo-1,8-naphthyridine-3-carboxylic acid;

7-(1,4-diazabicyclo[3.2.1]oct-4-yl)-1-ethyl-6,8-difluoro-1,4-dihydro-4-oxo-3-quinolinecarboxylic acid;

7-(1,4-diazabicyclo[3.2.1]oct-4-yl)-1-ethyl-6-fluoro-1,4-dihydro-4-oxo-1,8-naphthyridine-3-carboxylic acid;

7-(1,4-diazabicyclo[3.2.1]oct-4-yl)-1-cyclopropyl-6,8-difluoro-1,4-dihydro-4-oxo-3-quinolinecarboxylic acid;

7-(1,4-diazabicylo[3.2.1]oct-4-yl)-1-cyclopropyl-6-fluoro-1,4-dihydro-4-oxo-1,8-naphthyridine-3-carboxylic acid;

7-[3-endo-amino-8-azabicyclo(3.2.1)oct-8-yl]-1-ethyl-6-fluoro-1,4-dihydro-4-oxo-1,8-naphthyridine-3-carboxylic acid;

7-[3-endo-amino-8-azabicyclo(3.2.1)oct-8-yl]-1-ethyl-6,8-difluoro-1,4-dihydro-4-oxo-3-quinolinecarboxylic acid;

7-[3-endo-amino-8-azabicyclo(3.2.1)oct-8-yl]-1-cyclopropyl-6-fluoro-1,4-dihydro-4-oxo-1,8-naphthyridine-3-carboxylic acid;

7-[3-exo-amino-8-azabicyclo(3.2.1)oct-8-yl]-1-cyclopropyl-6-fluoro-1,4-dihydro-4-oxo-1,8-naphthyridine-3-carboxylic acid;

1-cyclopropyl-6-fluoro-1,4-dihydro-7-(5-methyl-2,5-diazabicyclo[2.2.2]oct-2-yl)-1,8-naphthyridine-3-carboxylic acid;

1-cyclopropyl-6-fluoro-1,4-dihydro-7-(5-methyl-2,5-diazabicyclo[2.2.1]hept-2-yl)-4-oxo-1,8-naphthyridine-3-carboxylic acid;

1-cyclopropyl-6,8-difluoro-1,4-dihydro-7-(5-methyl-2,5-diazabicyclo[2.2.1]hept-2-yl)-4-oxo-3-quinolinecarboxylic acid;

7-[2,5-diazabicyclo(2.2.1)hept-2-yl]-1-ethyl-6,8-difluoro-1,4-dihydro-4-oxo-3-quinolinecarboxylic acid;

7-[2,5-diazabicyclo(2.2.1)hept-2-yl]-1-ethyl-6-fluoro-1,4-dihydro-4-oxo-1,8-naphthyridine-3-carboxylic acid;

1-cyclopropyl-7-[2,5-diazabicyclo(2.2.1)hept-2-yl]-6-fluoro-1,4-dihydro-4-oxo-1,8-naphthyridine-3-carboxylic acid;

1-cyclopropyl-7-[2,5-diazabicyclo(2.2.1)hept-2-yl]-6,8-difluoro-1,4-dihydro-4-oxo-3-quinolinecarboxylic acid;

10-[2,5-diazabicyclo(2.2.1)hept-2-yl]-9-fluoro-2,3-dihydro-3-methyl-7-oxo-7H-pyrido(1,2,3-de)-1,4-benzoxazine-6-carboxylic acid;

1-ethyl-6,8-difluoro-1,4-dihydro-4-oxo-7-[5-(phenylmethyl)-2,5-diazabicyclo(2.2.1)hept-2-yl]-3-quinolinecarboxylic acid;

10-(2,5-diazabicyclo[2.2.2]oct-2-yl)-9-fluoro-2,3-dihydro-3-methyl-7-oxo-7H-pyrido[1,2,3-de]-1,4-benzoxazine-6-carboxylic acid;

1-cyclopropyl-6-fluoro-1,4-dihydro-7-[5-(2-hydroxyethyl)-2,5-diazabicyclo(2.2.2)oct-2-yl]-4-oxo-1,8-naphthyridine-3-carboxylic acid, and the pharmaceutically acceptable acid addition or base salts thereof.

The invention includes a process for preparing compounds of the formula:

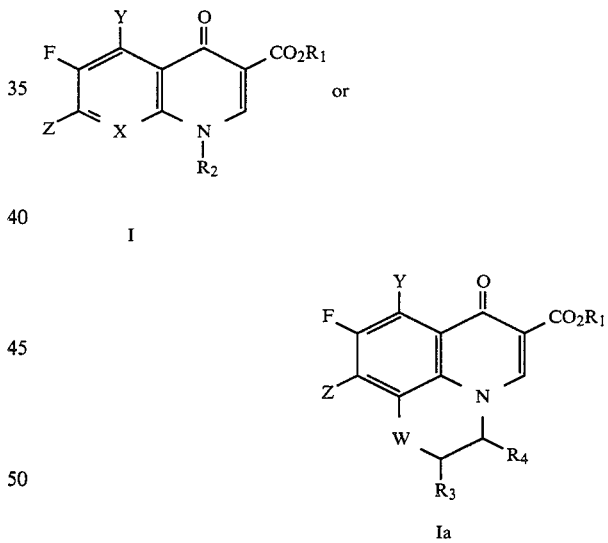

I

Ia wherein $R_1$, $R_2$, $R_3$, $R_4$, W, X, Y, and Z are as defined for formulae I and Ia which comprises reacting a compound having the following structural formula:

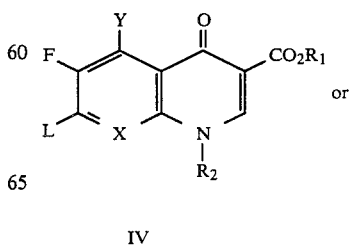

IV

-continued

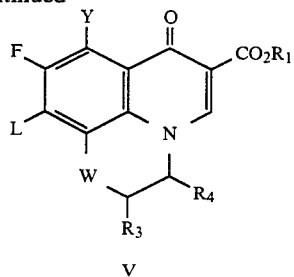

with an amine corresponding to the group Z wherein Z is a compound having the structural formula:

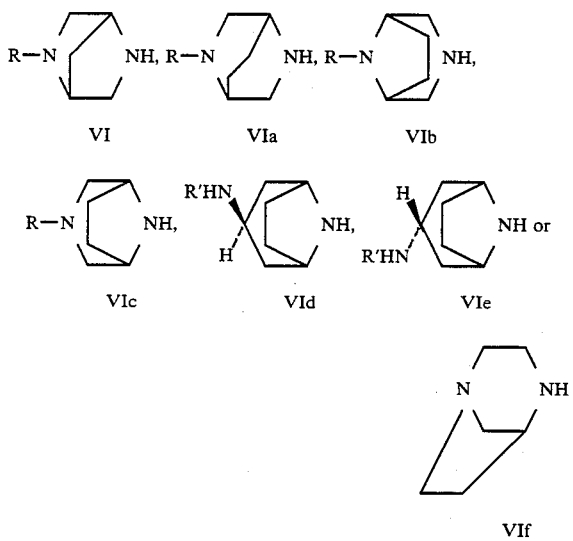

wherein all of the above terms are as defined in formulae I and Ia and L is a leaving group which is halogen or an alkylsulfonyl group of from one to three carbon atoms, preferably fluorine, chlorine, methane- or ethanesulfonyl.

The invention also includes a pharmaceutical composition which comprises an antibacterially effective amount of a compound having structural formula I or Ia and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the invention having the structural formulae III and IIIa may be readily prepared by treating a corresponding compound having the structural formula IV or V with the desired cyclic amine VI-f. For purposes of this reaction, the alkylamine substituent of compounds VI-f may, if desired, be protected by a group which renders it substantially inert to the reaction conditions. Thus, for example, protecting groups such as the following may be utilized: carboxylic acyl groups such as formyl, acetyl, trifluoroacetyl; alkoxycarbonyl groups such as ethoxycarbonyl, t-butoxycarbonyl, $\beta,\beta,\beta$-trichloroethoxycarbonyl, $\beta$-iodoethoxycarbonyl; aryloxycarbonyl groups such as benzyloxycarbonyl, p-methoxybenzyloxycarbonyl, phenoxycarbonyl; silyl groups such trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between compound IV or V and compounds VI-f, if desired, by procedures known to those skilled in the art. For example, the ethoxycarbonyl group may be removed by acid or base hydrolysis and the trityl group may be removed by hydrogenolysis.

The reaction between the compound of structural formula IV or V and a suitably protected compound of formula VI-f may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, 1,8-diazabicyclo[5.4.0]undec-7-ene (DBU), pyridine, or picoline. Alternatively an excess of a compound of formula VI-f may be utilized as the acid acceptor.

Convenient solvents for this reaction are non-reactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group may be accomplished either before or after isolating the product, III or IIIa. Alternatively, the protecting group need not be removed.

The starting compounds having structural formulae IV and V are known in the art or, if new, may be prepared from known starting materials by standard procedures or by variations thereof. Thus the following compounds are disclosed in the noted references:

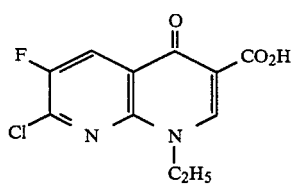

European Patent Application 80 40 1369

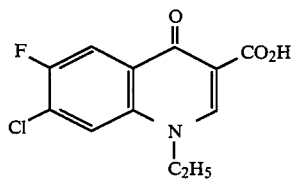

J. Med. Chem., 23, 1358 (1980)

-continued

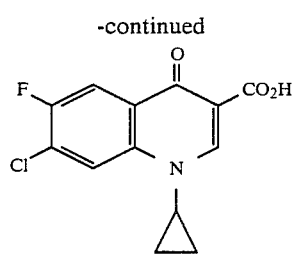

European Patent Application 0078362

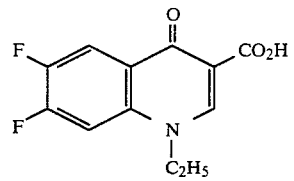

European Patent 0 000 203 (1979)

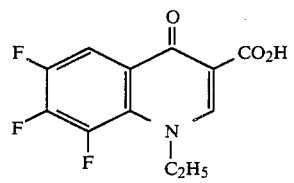

British Patent 2,057,440

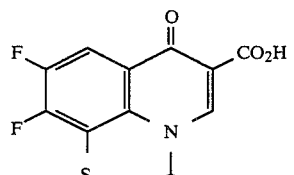

Japanese Patent Publication 7203-085

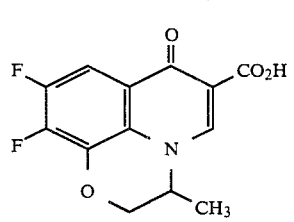

European Patent Application 81 10 6747

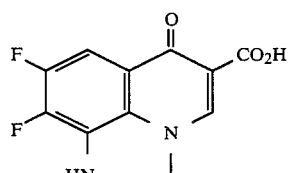

Japanese Patent Publication 7203-085

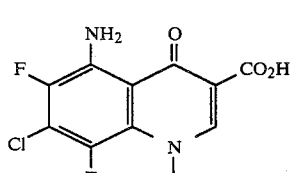

Japanese Patent Publication 8174 367-A

-continued

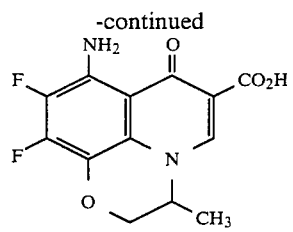

Japanese Patent Publication 7149-286

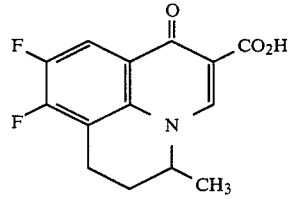

British Patent 2057 440

1-Cyclopropyl-6,7,8-trifluoro-1,4-dihydro-4-oxo-3-quinolinecarboxylic acid may be prepared by a series of reactions starting from 2,3,4,5-tetrafluorobenzoic acid. The sodium salt of 2,3,4,5-tetrafluorobenzoic acid is reacted with oxalyl chloride and the product condensed with diethyl malonate in the presence of magnesium turnings to afford after hydrolysis 2,3,4,5-tetrafluorobenzoylacetic acid, ethyl ester. This compound is, in turn, treated with triethylorthoformate and acetic anhydride, followed by cyclopropylamine to afford 2-(2,3,4,5-tetrafluorobenzoyl)-2-cyclopropylaminoacrylic acid, ethyl ester, which is then ring closed and hydrolysed with sodium hydride to give the desired intermediate.

7-Chloro-1-cyclopropyl-6-fluoro-1,4-dihydro-4-oxo-1,8-naphthyridine-3-carboxylic acid may be prepared by a series of reactions starting from 4-(6-chloro-3-nitro-2-pyridinyl)-1-piperazinecarboxylic acid, ethyl ester. The intermediate, 1-cyclopropyl-6-fluoro-1,4-dihydro-4-oxo-7-(1-piperazinyl)-1,8-naphthyridine-3-carboxylic acid can be converted to the 7-hydroxy derivative with a mixture of nitric and sulfuric acids which is then replaced by chlorine by treatment with phosphorus oxychloride to give the desired intermediate. The synthesis of both of the above N-cyclopropyl intermediates is described in the Preparative Examples.

The compounds of the invention having structural formula VI-f, are either known compounds or they may be prepared from known starting materials by standard procedures or by variations thereof. For example, exo and endo 3-amino-8-azabicyclo [3.2.1]octanes having the structural formula B and the acetyl derivatives E.

B

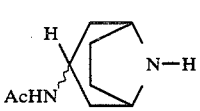

E may be readily prepared from the known starting material 8-(phenylmethyl)-8-azabicyclo[3.2.1]octan-3-one oxime, [J. R. Bagley and T. N. Riley, J. Heterocyclic Chem., 19, 485 (1982)] by the following reaction sequence.

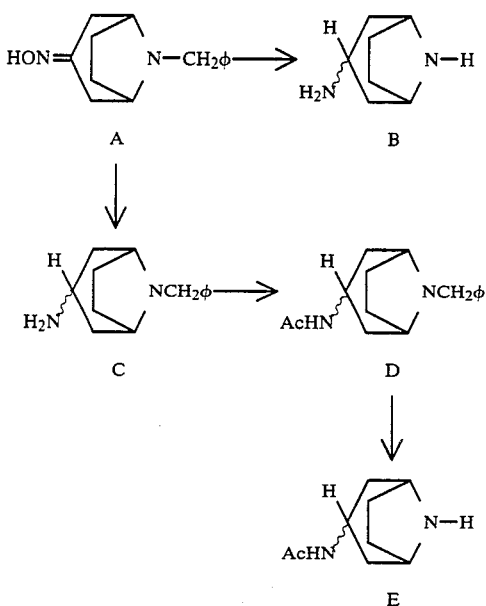

The compounds of the invention display antibacterial activity when tested by the microtitration dilution method as described in Heifetz, et al, Antimicr. Agents & Chemoth., 6, 124 (1974), which is incorporated herein by reference.

By use of the above reference method, the followed minimum inhibitory concentration value (MICs in μg/ml) shown in the table were obtained for representative compounds of the invention.

sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about three carbon atoms except when specifically stated to be greater than three carbon atoms. Representative of such groups are methyl, ethyl, propyl, isopropyl, and the like.

The cycloalkyl groups contemplated by the invention

| | IN VITRO ANTIBACTERIAL ACTIVITY Minimal Inhibitory Concentration MIC (μg/ml) | | | | | |
|---|---|---|---|---|---|---|
| Organisms | Compound Ex. 2 | Compound Ex. 3 | Compound Ex. 6a | Compound Ex. 7c | Compound Ex. 7d | Compound Ex. 10a |
| Enterobacter cloacae MA 2646 | 0.2 | 0.05 | 0.1 | 0.05 | 0.1 | <0.1 |
| Escherichia coli Vogel | 0.1 | 0.05 | 0.1 | 0.1 | 0.05 | 0.4 |
| Klebsiella pneumoniae MGH-2 | 0.4 | 0.1 | 0.05 | 0.05 | 0.1 | 0.4 |
| Proteus rettgeri M 1771 | 0.8 | 0.8 | 0.4 | 0.2 | 0.1 | 1.6 |
| Pseudomonas aeruginosa UI-18 | 0.4 | 0.8 | 0.2 | 0.1 | 0.2 | 1.6 |
| Staphylococcus aureus H 228 | 0.4 | 0.4 | 0.05 | 0.8 | 0.8 | 0.4 |
| Staphylococcus aureus UC-76 | ≦0.1 | 0.025 | 0.006 | 0.2 | 0.2 | 0.2 |
| Streptococcus faecalis MGH-2 | 1.6 | 1.6 | 0.4 | 0.8 | 0.8 | 1.6 |
| Streptococcus pneumoniae SV-1 | 0.8 | 1.6 | 0.4 | 0.8 | 1.6 | 1.6 |
| Streptococcus pyogenes C-203 | 0.4 | 0.8 | 0.4 | 0.2 | 0.2 | 1.6 |
| Organisms | Compound Ex. 10b | Compound Ex. 10c | Compound Ex. 14 | Compound Ex. 16 | Compound Ex. 17 | Compound Ex. 20 |
| Enterobacter cloacae MA 2646 | 0.1 | 0.1 | 0.1 | 0.5 | 0.025 | 0.8 |
| Escherichia coli Vogel | 0.05 | 0.05 | 0.05 | 0.1 | 0.05 | 0.4 |
| Klebsiella pneumoniae MGH-2 | 0.05 | 0.05 | 0.1 | 0.1 | 0.05 | 0.4 |
| Proteus rettgeri M 1771 | 0.4 | 0.2 | 0.4 | 0.2 | 0.2 | 0.8 |
| Pseudomonas aeruginosa UI-18 | 0.4 | 0.4 | 0.8 | 0.4 | 0.4 | 0.8 |
| Staphylococcus aureus H 228 | 0.4 | 0.1 | 0.8 | 0.4 | 0.4 | 0.4 |
| Staphylococcus aureus UC-76 | 0.1 | 0.025 | 0.1 | 0.1 | 0.025 | 0.2 |
| Streptococcus faecalis MGH-2 | 0.8 | 0.4 | 0.8 | 0.8 | 0.2 | 0.8 |
| Streptococcus pneumoniae SV-1 | 0.4 | 0.4 | 0.8 | 0.8 | 0.4 | 0.4 |
| Streptococcus pyogenes C-203 | 0.4 | 0.4 | 0.4 | 0.4 | 0.1 | 0.4 |

The compounds of the invention are capable of forming both pharmaceutically acceptable acid addition and/or base salts. Base salts are formed with metals or amines, such as alkali and alkaline earth metals or organic amines. Examples of metals used as cations are comprise those having three to six carbons atoms such as cyclopropyl, cyclobutyl, cyclopentyl, and cyclohexyl.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are β-fluoroethyl, β-chloroethyl, β,β-dichloroethyl, β-chloropropyl, β-chloro-2-propyl, γ-iodobutyl, and the like.

The term halogen is intended to include fluorine, chlorine, bromine, and iodine unless otherwise specified.

Certain compounds of the invention may exist in optically active forms. The pure D isomer, pure L isomer as well as mixtures thereof; including the racemic mixtures, are contemplated by the invention. Additional assymmetric carbon atoms may be present in a substituent such as an alkyl group. All such isomers as well as mixtures thereof are intended to be included in the invention.

The compounds of the invention can be prepared and administered in a wide variety of oral and paren-teral dosage forms. It will be obvious to those skilled in the art that the following dosage forms may comprise as the active component, either a compound of formula I or Ia or a corresponding pharmaceutically acceptable salt of a compound of formula I or Ia.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantites of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacter-ial infections the compounds utilized in the phar-maceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

PREPARATION OF STARTING MATERIALS

EXAMPLE A

1-Ethenyl-6,7,8-trifluoro-1,4-dihydro-4-oxo-3-quinolinecarboxylic acid 6,7,8-Trifluoro-1,4-dihydro-4-oxo-3-quinoline carboxylic acid ethyl ester is treated with dibromo ethane to afford the 1-ethenyl-6,7,8-trifluoro-1,4-dihydro-4-oxo-3-quinolinecarboxylic acid ester, mp 134°–135° C. Subsequent hydrolysis with hydrochloric acid gave 1-ethenyl-6,7,8-trifluoro-1,4-dihydro-4-oxo-3-quinolinecarboxylic acid, mp 186°–187° C.

EXAMPLE B 6,7,8-Trifluoro-1-(2-fluoroethyl)-1,4-dihydro-4-oxo-3-quinolinecarboxylic acid In identical fashion, 6,7,8-trifluoro-1,4-dihydro-4-oxo-3-quinoline carboxylic acid ethyl ester was converted with fluorobromoethane to 6,7,8-trifluoro-1-(2-fluoroethyl)-1,4-dihydro-4-oxo-3-quinoline carboxylic acid, m.p. 207°–211° C.

EXAMPLE C

1-Cyclopropyl-6,7,8-trifluoro-1,4-dihydro-4-oxo-3-quinolinecarboxylic acid 2,3,4,5-tetrafluorobenzoylacetic acid, ethyl ester To 25.2 g (0.117 mole) of sodium 2,3,4,5-tetrafluorobenzoate, prepared as a dry powder from 2,3,4,5-tetrafluorobenzoic acid [J. Org. Chem. 29, 2381 (1961)]and aqueous sodium hydroxide with concentration to dryness, was added 400 ml of dry ether and the suspension was cooled to 0° C. Slowly 25 ml (~2.5 equivalents) of oxalyl chloride in 50 ml of ether was added and the mixture brought to room temperature where it was maintained for 2.0 hours. It was filtered and concentrated to remove low boiling impurities. The residue was dissolved in 100 ml of ether and placed in an addition funnel.

Meanwhile, 2.9 g (0.119 mole) of magnesium turnings were treated with 100 ml of absolute ethanol and 0.3 ml of carbon tetrachloride. To this mixture was added 18.6 ml (0.12 mole) of diethyl malonate in 75 ml of ether at a rate to keep the temperature just below reflux. When addition was complete, the reaction was refluxed for two hours. At −20° C., the ethereal acid chloride was slowly added. When addition was complete, the reaction was brought to 0° C. over 18 hours. The mixture was poured into dilute hydrochloric acid and was extracted into dichloromethane which was dried (MgSO$_4$) and concentrated. The residue was then treated with 340 mg of p-toluenesulfonic acid in 600 ml of water at 100° C. for two hours with rapid stirring. The oil was extracted into dichloromethane, dried (MgSO$_4$) and concentrated. The residue was purified by column chromatography (Silica gel, using toluene:hexane: ether, 4:5:1), to give 18.5 g of a reddish oil. This material was triturated with pentane to give 10.2 g of 2,3,4,5-tetrafluorobenzoylacetic acid, ethyl ester, mp 49°–51° C.

2-(2,3,4,5-tetrafluorobenzoyl)-2-cyclopropylaminoacrylic acid, ethyl ester

To 10.16 g (38.5 mmole) of the 2-(2,3,4,5-tetrafluorobenzoylacetic acid, ethyl ester was added 8.43 g (57.0 mmole) of triethylorthoformate and 9.34 g (91.5 mmole) of acetic anhydride. The mixture was heated to 150° C. for two hours and was then placed under high vacuum at 75°–85° C. for one hour. The residue dissolved, without purification, in 100 ml of isopropyl alcohol and treated with 2.4 ml of cyclopropylamine. The reaction stood overnight. It was concentrated and purified by column chromatography (Silica gel 70–200, using hexane:chloroform:isopropyl alcohol, 80:15:5). The product off the column was recrystallized from pentane to give 6.16 g of 2-(2,3,4,5-tetrafluorobenzoyl)-2-cyclopropylaminoacrylic acid, ethyl ester, mp 63°–64° C.

1-Cyclopropyl-6,7,8-trifluoro-1,4-dihydro-4-oxo-3-quinolinecarboxylic acid

To 2.0 g (6.0 mmole) of the 2-(2,3,4,5-tetrafluorobenzoyl)-2-cyclopropylaminoacrylic acid, ethyl ester in 60 ml of dry dioxane was added 0.29 g of sodium hydride (50% dispersion) that was prewashed with pentane. The sodium hydride was delivered in 10 ml of dry tetrahydrofuran at 0° C. When evolution of hydrogen began to slow, the mixture was refluxed for two hours. It was concentrated, and the residue taken up in dichloromethane, which was water extracted, dried (MgSO$_4$) and concentrated. The residue was purified by column chromatography (Silica gel 70–200 mesh, using chloroform:hexane:isopropanol, 4:5:1) to give 0.95 g of the 1-cyclopropyl-6,7,8-trifluoro-1,4-dihydro-4-oxo-3-quinolinecarboxylic acid, ethyl ester, mp 168°–169° C. This material was dissolved in acetic acid at 100° C. and was treated with 10 ml of 0.5 N hydrochloric acid for 2.5 hours. The mixture was cooled and water added. The solids were then collected to give 0.7 g of 1-cyclopropyl-1,4-dihydro-4-oxo-6,7,8-trifluoro-3-quinolinecarboxylic acid, mp 226°–228° C.

EXAMPLE D

7-Chloro-1-cyclopropyl-6-fluoro-1,4-dihydro-4-oxo-1,8-naphthyridine-3-carboxylic acid 4-[6-(Cyclopropylamino)-3-nitro-2-pyridinyl]-1-piperazinecarboxylic acid, ethyl ester A solution of 126.0 g (0.4 mole) of 4-(6-chloro-3-nitro-2-pyridinyl)-1-piperazinecarboxylic acid, ethyl ester (prepared as described in European Patent Publication No. 9425), 76.1 g (0.5 mole) of 1,8-diazabicyclo[5.4.0]undec-7-ene (DBU), 28.6 g (0.5 mole) of cyclopropylamine and 500 ml of absolute ethanol was stirred at room temperature for 48 hours. The solution was then heated at reflux for four hours and concentrated in vacuo. The residue was partitioned between chloroform and water. The chloroform layer was dried over magnesium sulfate and concentrated in vacuo. The residue was triturated with ether to give 64.0 g of the title compound, mp 100°–103° C.

4-[6-(Acetylcyclopropylamino)-3-nitro-2-pyridinyl]-1-piperazinecarboxylic acid, ethyl ester A solution of 64.0 g (0.19 mole) of 4-[6-(cyclopropylamino)-3-nitro-2-pyridinyl]-1-piperazinecarboxylic acid, ethyl ester, 115 ml of acetic anhydride and 115 ml of acetic acid was heated on a steam bath for 36 hours. The solvents were removed in vacuo, the residue was triturated with a mixture of ethanol and toluene which was also evaporated in vacuo to give 68.3 g of the title compound, mp 90°–93° C.

4-[6-(Acetylcyclopropylamino)-3-amino-2-pyridinyl]-1-piperazinecarboxylic acid, ethyl ester A mixture of 17.0 g (45 mmole) of 4-[6-(acetylcyclopropylamino)-3-nitro-2-pyridinyl-1-piperazinecarboxylic acid, ethyl ester, 1.5 g of Raney nickel and 180 ml of absolute ethanol was shaken in a atmosphere of hydrogen at about 50 psi and room temperature for approximately 24 hours. The catalyst was removed by filtering through Celite and the solvent removed in vacuo to give 15.2 g of the title compound, mp 149°–150° C.

2-[4-(Ethoxycarbonyl)-1-piperazinyl]-6-(acetylcyclopropylamino)-3-pyridinediazonium tetrafluoroborate A solution of 20.8 g (60 mmole) of 4-(6-acetylcyclopropylamino)-3-amino-2-pyridinyl]-1-piperazinecarboxylic acid, ethyl ester, 44 ml of ethanol and 27 ml of 48% tetrafluoroboric acid was cooled to 0° C. and treated dropwise with a solution of 4.56 g (66 mmole) of sodium nitrite in 8 ml of water under a nitrogen atmosphere keeping the temperature 0°–5° C. After the addition was complete, the reaction was stirred at 0°–5° C. for one hour and treated with 150 ml of anhydrous ether keeping the temperature below 10° C. The solid was removed by filtration, the precipitate was washed with ethanol/ether (1:1), ether and dried in vacuo to give 24.5 g of the title compound, mp 100°–105° C. (dec.).

4-[6-(Acetylcyclopropylamino)-3-fluoro-2-pyridinyl]-1-piperazinecarboxylic acid, ethyl ester To 800 ml of refluxing toluene was added in portions, as a solid, 46.2 g (0.1 mole) of 2-[4-(ethoxycarbonyl)-1-piperazinyl]-6-(acetylcyclopropylamino)-3-pyridinediazonium tetrafluoroborate. borate. After the addition was complete, the reaction was refluxed for ten minutes and the toluene was decanted from the insoluble precipitate. The toluene was evaporated in vacuo and the residue was partitioned between chloroform and water. The chloroform layer was washed with 5% aqueous sodium bicarbonate, water, dried over magnesium sulfate and evaporated in vacuo to give 13.7 g of the title compound, as a viscous oil. An additional 10.2 g could be obtained by partitioning the original toluene insoluble material in chloroform and water. The organic layer was washed with 5% aqueous sodium bicarbonate, dried over magnesium sulfate, evaporated in vacuo and the residue was chromatographed on silica gel eluting with chloroform/ethyl acetate (6:4). This fraction was also a viscous oil which did not crystallize upon standing. Both fractions were of sufficient purity to be used as is in the ensuing steps.

4-[6-(Cyclopropylamino)-3-fluoro-2-pyridinyl]-1-piperazinecarboxylic acid, ethyl ester A solution of 21.9 g (63 mmole) of 4-[6-(acetylcyclopropylamino)-3-fluoro-2-pyridinyl]-1-piperazinecarboxylic acid, ethyl ester, 170 ml of 15% hydrochloric acid and 235 ml of methanol was refluxed for one hour and allowed to stir at room temperature for 18 hours. The methanol was removed in vacuo and the aqueous acid was made basic with 1.0 N sodium hydroxide to pH 10.5. The mixture was extracted with chloroform, the chloroform layer washed with water, dried over magnesium sulfate, and evaporated in vacuo to give 17.6 g of the title compound, mp 68°–70° C.

EXAMPLE E

1-Cyclopropyl-6-fluoro-1,4-dihydro-4-oxo-7-(1-piperazinyl)-1,8-naphthyridine-3-carboxylic acid Route A 1-[Cyclopropyl[6-[4-(ethoxycarbonyl)-1-piperazinyl]-5-fluoro-2-pyridinyl]amino]methylene]propanedioic acid, diethyl ester A solution of 3.8 g (12.3 mmole) of 4-[6-(cyclopropylamino)-3-fluoro-2-pyridinyl]-1-piperazinecarboxylic acid, ethyl ester, 2.7 g (12.3 mmole) of diethyl (ethoxymethylene)malonate and 50 ml of xylene was refluxed for 24 hours. The solvent was removed in vacuo and the residue was chromatographed over silica gel eluting with chloroform/ethyl acetate (80/20) to give 2.3 g of the title compound as a viscous oil which was used without further purification.

Ethyl 1-Cyclopropyl-6-fluoro-1,4-dihydro-4-oxo-7-[4-(ethoxycarbonyl)-1-piperazinyl]-1,8-naphthyridine-3-carboxylate A solution of 2.3 g (4.8 mole) of [[cyclopropyl[6-[4-(ethoxycarbonyl)-1-piperazinyl]-5-fluoro-2-pyridinyl]amino]methylene]propanedioic acid, diethyl ester, in 15 ml of acetic anhydride was treated dropwise with 5 ml of 98% sulfuric acid keeping the temperature 55°–60° C. When the addition was complete, the reaction was stirred for one hour and poured onto 50 g of ice. The aqueous suspension was extracted with chloroform, the chloroform layer washed with water, dried over magnesium sulfate, filtered, and evaporated in vacuo. The residue was triturated with several portions of ethanol/toluene which were also removed in vacuo to give 0.4 g of the title compound, mp 184°–186° C. An additional 0.5 g of product could be obtained by concentrating the original aqueous fraction, mp 184°–186° C.

1-Cyclopropyl-6-fluoro-1,4-dihydro-4-oxo-7-(1-piperazinyl)-1,8-naphthyridine-3-carboxylic acid A suspension of 0.7 g (1.6 mmole) of ethyl 1-cyclopropyl-6-fluoro-1,4-dihydro-4-oxo-7-[4-(ethoxycarbonyl)-1-piperazinyl]-1,8-naphthyridine-3-carboxylate, 6 ml of 10% aqueous sodium hydroxide and 2 ml of ethanol was refluxed for three hours. The reaction was filtered through a fiber glass pad to clarify and acidified to pH 1.5 with 6.0 M hydrochloric acid and lyophilized. The residue was dissolved in 10 ml of ammonium hydroxide and the solution concentrated in vacuo. The precipitate which formed was removed by filtration, washed with aqueous ethanol, ether and dried in vacuo to give 0.04 g, mp 274°–276° C.

Route B

4-[6-[Cyclopropyl(2,2-dimethyl-4,6-dioxo-1,3-dioxan-5-ylidine)amino]-3-fluoro-2-pyridinyl]-1-piperazinecarboxylic acid, ethyl ester A solution of 17.6 g (57 mmole) of 4-[6-(cyclopropylamino)-3-fluoro-2-pyridinyl]-1-piperazinecarboxylic acid, ethyl ester, 11.6 g (63 mmole) of 5-(methoxymethylene)-2,2-dimethyl-1,3-dioxane-4,6-dione and 250 ml of methanol was stirred at room temperature for four hours. The solid was removed by filtration, washed with methanol, ether and dried in vacuo to give 17.6 g of the title compound, mp 177°–178° C.

1-Cyclopropyl-6-fluoro-1,4-dihydro-4-oxo-7-[4-(ethoxycarbonyl)-1-piperazinyl]-1,8-naphthyridine-3-carboxylic acid A solution of 17.0 g (37.0 mmole) of 4-[6-(cyclopropyl(2,2-dimethyl-4,6-dioxo-1,3-dioxan-5-ylidene)amino]-3-fluoro-2-pyridinyl]-1-piperazinecarboxylic acid, ethyl ester in 125 ml of acetic anhydride was treated dropwise with 35 ml of 98% sulfuric acid keeping the temperature 50°–60° C. When the addition was complete, the reaction was stirred for two hours and poured onto 600 g of ice. The mixture was stirred was stirred for one hour and the resulting precipitate was removed by filtration, washed with water and dried in vacuo to give 10.2 g of the title compound, mp 277°–279° C.

1-Cyclopropyl-6-fluoro-1,4-dihydro-4-oxo-7-(1-piperazinyl)-1,8-naphthyridine-3-carboxylic acid A solution of 10.2 g (25 mmole) of 1-cyclopropyl-6-fluoro-1,4-dihydro-4-oxo-7-[4-(ethoxycarbonyl)-1-piperazinyl]-1,8-naphthyridine-3-carboxylic acid, 100 ml of 10% aqueous sodium hydroxide and 40 ml of ethanol was refluxed for three hours. The solution was concentrated to 125 ml and acidified to pH 7.3 with glacial acetic acid. The resulting precipitate was removed by filtration, washed with 50% aqueous ethanol, ether and dried in vacuo to give 7.2 g of the title compound, mp 274°–276°.

1-Cyclopropyl-6-fluoro-1,4-dihydro-7-hydroxy-4-oxo-1,8-naphthyridine-3-carboxylic acid To a solution of 2 ml of 70% nitric acid in 10 ml of 98% sulfuric acid was added in portions 1.0 g (3.0 mmole) of 1-cyclopropyl-6-fluoro-1,4-dihydro-4-oxo-7-(1-piperazinyl)-1,8-naphthyridine-3-carboxylic acid, keeping the temperature between 25°–30° C. The resulting solution was stirred at room temperature for 18 hours and poured onto 40 g of ice. The mixture was stirred at room temperature for 24 hours, concentrated in vacuo, the pH adjusted to 12 with aqueous sodium hydroxide, and filtered through a fiber glass pad. The filtrate was acidified to pH 3.5 with 6.0 M hydrochloric acid, the resulting precipitate removed by filtration, washed with water then ether and dried in vacuo to give 0.23 g of the title compound, mp 325°–327° C.

7-Chloro-1-cyclopropyl-6-fluoro-1,4-dihydro-4-oxo-1,8-naphthyridine-3-carboxylic acid A suspension of 0.19 g (0.72 mmole) of 1-cyclopropyl-6-fluoro-1,4-dihydro-7-hydroxy-4-oxo-1,8-naphthyridine-3-carboxylic acid in 2 ml of phosphorus oxychloride was heated at reflux for ½ hour. The resulting solution was cooled to room temperature and the solvent was removed in vacuo. The residue was triturated with ice-water and the resulting solid was removed by filtration, washed with water, then ether and dried in vacuo to give 0.11 g of the title compound, mp 209°–212° C.

EXAMPLE F

3-Endo(acetylamino)-8-azabicyclo[3.2.1]octane hydrochloride

3-Endo(acetylamino)-8-(phenylmethyl)-8-azabicyclo-[3.2.1]octane, hydrochloride

A solution of 6.2 g (28 mmole) of 3-(endo-amino) 8-(phenylmethyl)-8-azabicyclo[3.2.1]octane [J. R. Bagley and T. N. Riley, J. Heterocyclic Chem., 19, 485 (1982)], 2.84 ml (40 mmole) of acetyl chloride and 50 ml of acetonitrile was stirred at room temperature for two hours. The reaction mixture was filtered to give 3.70 g of the title compound, mp 203°–204° C.

3-Endo(acetylamino)-8-azabicyclo [3.2.1]octane, hydrochloride

A mixture of 3.58 g (11.2 mmole) of 3-endo(acetylamino)-8-(phenylmethyl)-8-azabicyclo[3.2.1]octane hydrochloride, 0.4 g of 20% palladium on carbon and 100 ml of methanol was hydrogenated until the requisite uptake was observed. The reaction mixture was filtered and the filtrate was evaporated to dryness to give 2.79 g of the title compound which was used without further purification.

EXAMPLE G

3-Exo(acetylamino)-8-(phenylmethyl)-8-azabicyclo[3.2.1]octane, hydrochloride

A solution of 4.6 g (20 mmole) of 3-(exo-amino)-8-phenylmethyl)-8-azabicyclo[3.2.1]octane [J. R. Bagley and T. N. Riley, J. Heterocyclic Chem., 19, 485 (1982)], 10 ml of acetic anhydride and 100 ml of acetic acid was heated under reflux for two hours. The reaction mixture was evaporation and the residue was dissolved in acetonitrile and 6 N HCl in 2-propanol. The solution was filtered and the filtrate was evaporated. The residue was recrystallized from acetonitrile-ethyl acetate to give 2.30 g of the title compound, mp 217°–219° C.

3-Exo(acetylamino)-8-azabicyclo[3.2.1]octane, hydrochloride

A mixture of 2.23 g (7.56 mmole) of 3-exo(acetylamino)-8-(phenylmethyl)-8-azabicyclo[3.2.1]octane, hydrochloride, 0.2 g of 20% palladium on carbon and 100 ml of methanol was hydrogenated until the requisite amount of hydrogen was taken up. The reaction mixture was filtered and the filtrate was evaporated to yield 1.5 g of the title compound which was used without further purification.

EXAMPLE H 3-(Exo-amino)-8-azabicyclo[3.2.1]octane, dihydrochloride

A mixture of 4.6 g (20 mmole) of 8-(phenylmethyl)-8-azabicyclo[3.2.1]octan-3-one, oxime [J. R. Bagley and T. N. Riley, J. Heterocyclic Chem., 19, 485 (1982)], 0.5 g of 10% rhodium on carbon, and 100 ml of acetic acid was hydrogenated until the requisite amount of hydrogen was taken up. The reaction mixture was filtered and two equivalents of HCl was added. The solid was filtered to yield 2.80 g of the title compound, mp > 300° C.

EXAMPLE I 3-(Endo-amino)-8-azabicyclo[3.2.1]octane, dihydrochloride

A solution of 7.33 g (25 mmol) of 3-(endoamino)-8-(phenylmethyl)-8-azabicyclo[3.2.1]octane dihydrochloride [P. Dostert et al, Eur. J. Med. Chem.-Chim. Ther., 19, 105 (1984)], 1.0 g of 20% palladium on carbon and 100 ml of methanol was hydrogenated until the required amount of hydrogen was taken up. The reaction mixture was filtered and the filtrate was evaporated to 4.5 g of the title compound which was used without purification.

EXAMPLE J

1-Cyclopropyl-7-(ethylthio)-6-fluoro-1,4-dihydro-4-oxo-1,8-naphthyridine-3-carboxylic acid A solution of 3.40 g (12 mmol) 1-cyclopropyl-7-chloro-6-fluoro-4-oxo-1,4-dihydro-1,8-naphthyridine-3-carboxylic acid in 60 ml N,N-dimethylformamide heated to 60° C. was treated with a solution of 3.36 g (60 mmol) potassium hydroxide and 6 ml (81 mmol) ethanethiol in 30 ml absolute ethanol. After stirring 15 minutes at 60° C. the mixture was poured into 240 ml ice cold 0.5 N hydrochloric acid, and the precipitate was filtered, washed with water and crystallized from acetic acid—water to give 3.10 g, mp 242°–244° C. of the title compound.

1-Cyclopropyl-7-(ethanesulfonyl)-6-fluoro-1,4-dihydro-4-oxo-1,8-naphthyridine-3-carboxylic acid A solution of 0.20 g (0.65 mmol) 1-cyclopropyl-7-(ethylthio)-6-fluoro-4-oxo-1,4-dihydro-1,8-naphthyridine-3-carboxylic acid in 2 ml trifluoroacetic acid was stirred in an ice bath and treated dropwise with 0.4 ml 30% hydrogen peroxide. The bath was removed, stirring continued 4.75 hours, and the mixture poured into ice water. Filtration afforded 0.20 g of the title compound, mp 240°–242° C.

EXAMPLE K

1-Ethyl-7-(ethylthio)-6-fluoro-1,4-dihydro-4-oxo-1,8-naphthyridine-3-carboxylic acid A suspension of 0.54 g (2 mmol) 1-ethyl-7-chloro-6-fluoro-4-oxo-1,4-dihydro-1,8-naphthyridine-3-carboxylic acid in 10 ml N,N-dimethyl formamide was stirred at 60° C. and treated all at once with a solution of 0.56 g potassium hydroxide (10 mmol) and 1 ml (0.85 mmol) ethanethiol in 5 ml absolute ethanol. After 15 minutes the mixture was poured into 40 mmol 0.4 N hydrochloric acid containing ice. The precipitate was filtered, washed with ethanol and ether to afford 0.46 g of the title compound. A sample for analysis was crystallized from acetic acid, mp 219°–221° C.

1-Ethyl-7(ethanesulfonyl)-6-fluoro-1,4-dihydro-4-oxo-1,8-naphthyridine-3-carboxylic acid A solution of 3.29 g (11 mmol) 1-ethyl-7-(ethylthio)-6-fluoro-1,4-dihydro-4-oxo-1,8-naphthyridine-3-carboxylic acid in 30 ml trifluoroacetic acid stirred in an ice bath was heated dropwise with 6.6 ml (73 mmol) 30% hydrogen peroxide. The bath was removed and stirring was continued at room temperature for 4.75 hours. The mixture was prepared into 300 ml ice water and the precipitate filtered to afford 3.46 g of the title compound, mp 249°–252° C.

EXAMPLE 1

7-(2,5-Diazabicyclo[2.2.2]oct-2-yl)-1-ethyl-6-fluoro-1,4-dihydro-4-oxo-3-quinolinecarboxylic acid A solution of 0.52 g (2.0 mmole) of 1-ethyl-6,7-difluoro-1,4-dihydro-4-oxo-3-quinolinecarboxylic acid, 0.37 g (2.0 mmole) of 2,5-diazabicyclo(2.2.2)octane dihydrochloride [P. A. Sturm et al., J. Med. Chem., 17, 481 (1974)], 0.90 ml (6.0 mmole) of 1,8-diazabicyclo[5.4.0]undec-7-ene and 25 ml of acetonitrile was heated under reflux for 21 hours. The reaction mixture was filtered and the filtrate was evaporated to dryness. The residue was recrystallized from ethanol to give 0.30 g of the title compound, mp 270°–272°.

EXAMPLE 2

7-(2,5-Diazabicyclo[2.2.2]oct-2-yl)-1-ethyl-6,8-difluoro-1,4-dihydro-4-oxo-3-quinolinecarboxylic acid A solution of 0.81 g (3.0 mmole) of 1-ethyl-6,7,8-trifluoro-1,4-dihydro-4-oxo-3-quinolinecarboxylic acid, 0.74 g (4.0 mmole) of 2,5-diazabicyclo[2.2.2]octane dihydrochloride [P. A. Sturm et al., J. Med. Chem., 17, 481 (1974)], 1.65 ml (11 mmole) of 1,8-diazabicyclo[5.4.0]undec-7-ene, and 40 ml of acetonitrile was stirred at room temperature for 25 hours and heated under reflux for two hours. The reaction mixture was filtered and the solid was washed with methanol to give 0.68 g of the title compound, mp 255°–257°.

EXAMPLE 3

7-(2,5-Diazabicyclo[2.2.2]oct-2-yl)-1-cyclopropyl-6,8-difluoro-1,4-dihydro-4-oxo-3-quinolinecarboxylic acid A mixture of 0.28 g (1 mmole) of 1-cyclopropyl-6,7,8-trifluoro-1,4-dihydro-4-oxo-3-quinolinecarboxylic acid, 0.2 g (1.1 mmole) 2,5-diazabicyclo[2.2.2]octane dihydrochloride [P. A. Sturm et al., J. Med. Chem., 17, 481 (1974)], 0.45 ml (3.0 mmole) of 1,8-diazabicyclo[5.4.0]undec-7-ene and 10 ml of acetonitrile was heated at reflux for four hours. After cooling to room temperature, the reaction mixture was filtered and the solid washed with ethanol and dried to give 0.27 g of the title compound, mp 275°–280° C.

EXAMPLE 4

7-(2,5-Diazabicyclo[2.2.2]oct-2-yl)-1-ethyl-6-fluoro-1,4-dihydro-4-oxo-1,8-naphthyridine-3-carboxylic acid A solution of 0.54 g (2.0 mmole) of 7-chloro-1-ethyl-6-fluoro-1,4-dihydro-4-oxo-1,8-naphthyridine-3-carboxylic acid, 0.46 g (2.5 mmole) of 2,5-diazabicyclo[2.2.2]octane dihydrochloride [P. A. Sturm et al., J. Med. Chem., 17, 481 (1974)], 1.05 ml (7.0 mmole) of 1,8-diazabicyclo (5.4.0) undec-7-ene, and 30 ml of acetonitrile was stirred at room temperature for 23 hours. The reaction mixture was filtered and the solid was washed with acetonitrile to give 0.63 g of the title compound, mp 250°–253°.

EXAMPLE 5

10-(2,5-Diazabicyclo[2.2.2]oct-2-yl)-9-fluoro-2,3-dihydro-3-methyl-7-oxo-7H-pyrido[1,2,3-de]-1,4-benzoxazine-6-carboxylic acid A solution of 0.56 g (2.0 mmol) of 9,10-difluoro-2,3-dihydro-3-methyl-7-oxo-7H-pyrido[1,2,3-de]-1,4-benzoxazine-6-carboxylic acid, 0.41 g (2.2 mmol) of 2,5-diazabicyclo[2.2.2]octane dihydrochloride, 0.90 ml (6.0 mmol) of 1,8-diazabicyclo[5.4.0]undec-7-ene, and 25 ml of acetonitrile was heated under reflux for 18 hours. The solution was evaporated to dryness and the residue was triturated with methanol and filtered to give 0.20 g of the title compound, 260°–265° C.

EXAMPLE 6

In the same manner as Examples 1–5, the following compounds are prepared from 2,5-diazabicyclo[2.2.2]octane dihydrochloride and the appropriate quinoline or naphthyridine intermediate:

7-(2,5-diazabicyclo[2.2.2]oct-2-yl)-1-cyclopropyl-6-fluoro-1,4-dihydro-4-oxo-1,8-naphthyridine-3-carboxylic acid (a); mp 265°–270° C., 7-(2,5-diazabicyclo[2.2.2]oct-2-yl)-1-ethenyl-6,8-difluoro-1,4-dihydro-4-oxo-3-quinolinecarboxylic acid (b), and 7-(2,5-diazabicyclo[2.2.2]oct-2-yl)-(2-fluoro-ethyl)-6,8-difluoro-1,4-dihydro-4-oxo-3-quinolinecarboxylic acid (c).

EXAMPLE 7

7-[2,5-Diazabicyclo(2.2.1)hept-2-yl]-1-ethyl-6,8-difluoro-1,4-dihydro-4-oxo-3-quinolinecarboxylic acid (a)

A solution of 0.54 g (2.0 mmol) of 1-ethyl-6,7,8-trifluoro-1,4-dihydro-4-oxo-3-quinolinecarboxylic acid, 0.57 g (2.2 mmol) of 2,5-diazabicyclo(2.2.1)heptane dihydrobromide [P. S. Portoghese and A. A. Mikhail, J. Org. Chem., 31, 1059 (1966)], 0.90 ml (6.0 mmol) of 1,8-diazabicyclo(5.4.0)undec-7ene, and 20 ml of acetonitrile was heated under reflux for one hour and stirred at room temperature for two hours. The reaction mixture was filtered and the solid was washed with ethanol to give 0.60 g of the title compound, mp 275° C.

In a similar manner the following compounds were prepared:

7-[2,5-diazabicyclo(2.2.1)hept-2-yl]-1-ethyl-6-fluoro-1,4-dihydro-4-oxo-1,8-naphthyridine-3-carboxylic acid (b), mp 233°–6° C., 1-cyclopropyl-7-[2,5-diazabicyclo(2.2.1)hept-2-yl]-6-fluoro-1,4-dihydro-4-oxo-1,8-naphthyridine-3-carboxylic acid, monohydrochloride (c), mp 257°–9° C., 1-cyclopropyl-7-[2,5-diazabicyclo(2.2.1)hept-2-yl]-6,8-difluoro-1,4-dihydro-4-oxo-3-quinolinecarboxylic acid (d), mp 295° C., and 10-[2,5-diazabicyclo(2.2.1)hept-2-yl]-9-fluoro-2,3-dihydro-3-methyl-7-oxo-7H-pyrido(1,2,3-de)-1,4-benzoxazine-6-carboxylic acid (e), mp 265°–270° C.

EXAMPLE 8

1-Ethyl-6,8-difluoro-7-(5-methyl-2,5-diazabicyclo-[2.2.2]oct-2-yl)-1,4-dihydro-4-oxo-3-quinolinecarboxylic acid, hydrochloride A solution of 1.15 g (3.0 mmole) of 7-(2,5-diazabicyclo [2.2.2]oct-2-yl)-1-ethyl-6,8-difluoro-1,4-dihydro-4-oxo-3-quinolinecarboxylic acid, 10 ml of 37% formaldehyde solution, and 10 ml of 88% formic acid was heated under reflux for four hours. The reaction mixture was evaporated to dryness, 1 ml of 6 N hydrogen chloride in 2-propanol and 25 ml of alcohol was added and the mixture was heated. The solid was filtered off and washed with ethanol to give 0.98 g of the title compound, mp>300°.

EXAMPLE 9

1-Cyclopropyl-6-fluoro-1,4-dihydro-7-(5-methyl-2,5-diazabicyclo[2.2.2]oct-2-yl)-1,8-naphthyridine-3-carboxylic acid monohydrochloride A solution of 0.77 g (2.0 mmol) of 1-cyclopropyl-6-fluoro-1,4-dihydro-7-(2,5-diazabicyclo[2.2.2]oct-2-yl)-1,8-naphthyridine-3-carboxylic acid, 10 ml of 88% formic acid, and 10 ml of 37% formaldehyde solution was heated under reflux for four hours. After stirring the solution at room temperature overnight, it was evaporated to dryness, and the residue was treated with 6 N HCl in 2-propanol and ethanol. The solid was collected to give 0.45 g of the title compound, mp>310° C.

EXAMPLE 10

1-Ethyl-6-fluoro-7-(5-methyl-2,5-diazabicyclo[2.2.2]oct-2-yl)-1,4-dihydro-4-oxo-1,8-naphthyridine-3-carboxylic acid hydrochloride (a)

A solution of 1.16 g (3.18 mmole) of 7-(2,5-diazabicyclo[2.2.2]oct-2-yl)-1-ethyl-6-fluoro-1,4-dihydro-4-oxo-1,8-naphthyridine-3-carboxylic acid, 10 ml of 37% formaldehyde solution; and 10 ml of 88% formic acid was heated under reflux for four hours. The reaction mixture was evaporated to dryness and 1 ml of 6 N hydrogen chloride in 2-propanol and 25 ml of ethanol was added to the residue. After heating this mixture the solid was filtered off. The solid was dissolved with 1N sodium hydroxide and precipitated with 1N hydrochloric acid at pH 1.5 to give 0.22 g of the title compound, mp>300°.

In a similar manner the following compounds were prepared:

1-cyclopropyl-6-difluoro-1,4-dihydro-7-(5-methyl-2,5-diazabicyclo[2.2.1]hept-2-yl)-4-oxo-1,8-naphthyridine-3-carboxylic acid monohydrochloride (b), mp ~310° C. dec., 1-cyclopropyl-6,8-difluoro-1,4-dihydro-7-(5-methyl-2,5-diazabicyclo[2.2.1]hept-2-yl)-4-oxo-3-quinolinecarboxylic acid monohydrochloride (c), mp 297°–299° C. dec., and 1-ethyl-6,8-difluoro-7-(5-methyl-2,5-diazabicyclo[2.2.1]hept-2-yl)-1,4-dihydro-4-oxo-3-quinolinecarboxylic acid, hydrochloride (d), mp>300° C.

EXAMPLE 11

1-Ethyl-7-(5-ethyl-2,5-diazabicyclo[2.2.2]-oct-2-yl)-6-fluoro-1,4-dihydro-4-oxo-1,8-naphthyridine-3-carboxylic acid, hydroiodide A solution of 0.35 g (1.0 mmole) of 7-(2,5-diazabicyclo[2.2.2]oct-2-yl)-1-ethyl-6-fluoro-1,4-dihydro-4-oxo-1,8-naphthyridine-3-carboxylic acid, 0.32 ml (4.0 mmole) of ethyl iodide, 0.56 ml (4.0 mmole) triethylamine and 10 ml of N, N-dimethylformamide was heated at 100° for 17 hours. The reaction mixture was evaporated to dryness and the residue was stirred with 25 ml of 1 N sodium hydroxide for one hour. The solution was neutralized to pH 7 with 1 N hydrochloric acid, filtered and evaporated the filtrate to dryness. The residue was recrystallized from ethanol to give 0.29 g of the title compound, mp>300°.

In the same manner the following compounds are prepared:

1-ethyl-7-[5-ethyl-2,5-diazabicyclo[2.2.1]-hept-2-yl]-6,8-difluoro-1,4-dihydro-4-oxo-3-quinolinecarboxylic acid, hydrochloride, mp 240°–250° C. dec (b), and 1-ethyl-7-[5-(1-methylethyl)-2,5-diazabicyclo[2.2.1]hept-2-yl]6,8-difluoro-1,4-dihydro-4-oxo-3-quinolinecarboxylic acid, hydrochloride, (c).

EXAMPLE 12

1-Cyclopropyl-6-fluoro-1,4-dihydro-7-[5-(2-hydroxyethyl)-2,5-diazabicyclo(2.2.2)oct-2-yl]-4-oxo-1,8-naphthyridine-3-carboxylic acid, monohydrobromide A solution of 0.77 g (2.0 mmol) of 7-(2,5-diazabicyclo[2.2.2]oct-2-yl)-1-cyclopropyl-6-fluoro-1,4-dihydro-4-oxo-1,8-naphthyridine-3-carboxylic acid, 0.70 ml (8.0 mmol) of 2-bromoethanol, 1.30 ml (8.0 mmol) of triethylamine, and 20 ml of DMF was heated at 100° C. for 18 hours. The reaction solution was evaporated to dryness and the residue was triturated ethanol. The solid was collected by filtration to give 0.61 g of the title product, mp 290° C. dec (a).

In the same manner the following compound was prepared:

1-ethyl-6,8-difluoro-1,4-dihydro-7-[5-(2-hydroxyethyl)-2,5-diazabicyclo[2.2.1]hept-2-yl]-4-oxo-3-quinolinecarboxylic acid, monohydrobromide (b), mp 242°–245° C. dec.

EXAMPLE 13

1-Ethyl-6,8-difluoro-1,4-dihydro-4-oxo-7-[5-(phenylmethyl)-2,5-diazabicyclo(2.2.1)hept-2-yl]-3-quinolinecarboxylic acid A solution of 0.54 g (2.0 mmol) of 1-ethyl-6,7,8-trifluoro-1,4-dihydro-4-oxo-3-quinolinecarboxylic acid, 0.77 g (2.2 mmol) of 5-(phenylmethyl)-2,5-diazabicyclo(2.2.1)heptane dihydrobromide, (P. S. Portoghese and A. A. Mikhail, J. Org. Chem. 31, 1059 (1966)], 0.90 ml (6.0 mmol) of 1,8-diazabicyclo(5.4.0)undec-7-ene, and 20 ml of acetonitrile was heated under reflux for two hours and stirred at room temperature for two days. The mixture was filtered and the solid was washed with methanol to give 0.44 g of the title compound, mp 195°–198° C.

EXAMPLE 14

1-Cyclopropyl-7-(1,4-diazabicyclo[3.2.1]oct-4-yl-6-fluoro-4-oxo-1,4-dihydro-1,8-naphthyridine-3-carboxylic acid A suspension of 2.67 g (7.85 mmol) 1-cyclopropyl-7-ethanesulfonyl-6-fluoro-4-oxo-1,4-dihydro-1,8-naphthyridine-3-carboxylic acid and 1.58 g (8.54 mmol) 1,4-diazabicyclo[3.2.1]octane dihydrochloride (P. A. Strum, et al, J. Med. Chem., 20 1333 (1977)] in 40 ml acetonitrile was treated at 0° C. with 3.86 g (25.4 mmol) 1,8-diazabicyclo[5.4.0]undec-7-ene and the resulting solution stirred 18 hours at room temperature. Filtration of the precipitate afforded 1.04 g of the title compound, mp 276°–278° C. with decomposition.

EXAMPLE 15

1-Ethyl-7-(1,4-diazabicyclo[3.2.1]oct-4-yl)-6-fluoro-4-oxo-1,4-dihydro-1,8-naphthyridine-3-carboxylic acid A suspension of 2.06 g (6.28 mmol) 1-ethyl-7-ethanesulfonyl-6-fluoro-4-oxo-1,4-dihydro-1,8-naphthyridine-3-carboxylic acid and 1.29 g (6.97 mmol) 1,4-diazabicyclo[3.2.1]octane dihydrochloride in 30 ml acetonitrile was treated with 3.10 g (20.4 mmol) 1,8-diazabicyclo[5.4.0]undec-7-ene. The resulting solution was stirred overnight and the precipitate which formed was filtered to afford 0.40 g of the title compound, mp 228°–229° C.

EXAMPLE 16

7-(1,4-Diazabicyclo[3.2.1]oct-4-yl)-1-ethyl-6,8-difluoro-1,4-dihydro-4-oxo-3-quinolinecarboxylic acid To a solution of 0.81 g (3 mmole) 1-ethyl-6,7,8-trifluoro-4-oxo-1,4-dihydro-3-quinolinecarboxylic acid and 0.46 g (3 mmole) 1,8-diazabicyclo[5.4.0]undec-7-ene in 10 ml acetonitrile was added 0.37 g (3.3 mmole) 1,4-diazabicyclo[3.2.1]octane and the mixture stirred at reflux 5½ hours. After standing overnight at room temperature a yellowish solid was filtered, washed with acetonitrile and ether and dried in vacuo to afford 0.22 g product, mp decomposed above 233° C.

EXAMPLE 17

1-Cyclopropyl-7-(1,4-diazabicyclo[3.2.1]oct-4-yl)-6,8-difluoro-1,4-dihydro-4-oxo-3-quinolinecarboxylic acid A mixture of 1.14 g (4 mmol) 1-cyclopropyl-6,7,8-trifluoro-4-oxo-1,4-dihydro-3-quinolinecarboxylic acid, 0.62 g (5.5 mmol) 1,4-diazabicyclo[3.2.1]octane and 0.40 g (4 mmol) 1,8-diazabicyclo[5.4.0]undec-7-ene in 20 ml acetonitrile was refluxed 6.5 hours. After cooling to room temperature the solid product was filtered, suspended in 10 ml hot ethanol, cooled, and filtered to afford 0.55 g of 1-cyclopropyl-7-(1,4-diazabicyclo[3.2.1]octan-4-yl)-6,8-difluoro-1,4-dihydro-4-oxo-3-quinolinecarboxylic acid, mp 280° C. (dec).

EXAMPLE 18

1-Ethyl-6,8-difluoro-1,4-dihydro-7-(8-methyl-3,8-diazabicyclo[3.2.1]oct-2-yl)-4-oxo-3-quinolinecarboxylic acid (a)

A mixture of 1.40 g (5.0 mmole) of 1-ethyl-6,7,8-trifluoro-1,4-dihydro-4-oxo-3-quinolinecarboxylic acid, 2.0 g (8 mmole) of 8-methyl-3,8-diazabicyclo[3.2.1]octane dihydrochloride [P. A. Sturm et al., J. Med. Chem., 17, 481 (1974)], 2.0 ml (13.3 mmole) of 1,8-diazobicyclo[5.4.0]undec-7-ene, and 75 ml of acetonitrile was heated under reflux for 1.5 hr and then stirred at room temperature for 22 hours. The reaction mixture was evaporated to dryness and the residue was recrystallized from 2-propanol to give 0.84 g of the title compound, mp 184°–187° C.

In the same manner, the following compounds are prepared from 8-methyl-3,8-diazabicyclo[3.2.1]octane dihydrochloride:

1-cyclopropyl-6,8-difluoro-1,4-dihydro-7-(8-methyl-3,8-diazabicyclo[3.2.1]oct-2-yl)-4-oxo-3-quinolinecarboxylic acid (b), and 1-cyclopropyl-6-fluoro-1,4-dihydro-7-(8-methyl-3,8-diazabicyclo[3.2.1]oct-2-yl)-4-oxo-1,8-naphthyridine-3-carboxylic acid (c).

EXAMPLE 19

1-Ethyl-6-fluoro-1,4-dihydro-7-(3-methyl-3,8-diazabicyclo[3.2.1]oct-2-yl)-4-oxo-1,8-naphthyridine-3-carboxylic acid, hydrochloride (a)

A mixture of 0.54 g (2.0 mmol) of 7-chloro-1-ethyl-6-fluoro-1,4-dihydro-4-oxo-1,8-naphthyridine-3-carboxylic acid, 0.50 g (2.5 mmol) of 3-methyl-3,8-diazabicyclo[3.2.1]octane dihydrochloride [P. A. Sturm, et al, J. Med. Chem., 17, 481 (1974)], 0.75 ml (5.0 ml) 1,8-diazabicyclo[5.4.0]undec-7-ene and 20 ml of acetonitrile was heated under reflux for 1.5 hours and stirred overnight at room temperature. The reaction mixture was filtered and the solid washed with ethanol to give 0.46 g of the title compound, mp>310°.

In the same manner, the following compounds are prepared from 3-methyl-3,8-diazabicyclo [3.2.1]octane dihydrochloride and the appropriate quinoline or naphthyridine intermediate:

1-cyclopropyl-6,8-difluoro-1,4-dihydro-7-(3-methyl-3,8-diazabicyclo[3.2.1]oct-2-yl)-4-oxo-3-quinolinecarboxylic acid (b), and 1-cyclopropyl-6-fluoro-7-(3-methyl-3,8-diazabicyclo[3.2.1]oct-2-yl)-1,4-dihydro-4-oxo-1,8-naphthyridine-3-carboxylic acid (c).

EXAMPLE 20

7-(3-(Exo-amino)-8-azabicyclo[3.2.1]oct-8-yl]-1-ethyl-6-fluoro-1,4-dihydro-4-oxo-1,8-naphthyridine-3-carboxylic acid, hydrochloride A solution of 0.81 g (3.0 mmole) of 7-chloro-1-ethyl-6-fluoro-1,4-dihydro-4-oxo-1,8-naphthyridine-3-carboxylic acid, 1.0 g (5 mole) of 3-(exo-amino)-8-azabicyclo[3.2.1]octane, dihydrochloride, 1.35 ml (9.0 mole) of 1,8-diazabicyclo[5.4.0]undec-7-ene, and 30 ml of acetonitrile was heated under reflux for two hours and stirred at room temperature for 19 hours. The reaction mixture was filtered and the solid was dissolved in 20 ml of 0.5 N sodium hydroxide. The solution was acidified to pH 8 and filtered and the filtrate was further acidified to pH 2. The solid was collected by filtration to give 0.35 g of the title compound, mp~300°.

EXAMPLE 21

7-[3-Exo-amino)-8-azabicyclo[3.2.1]oct-8-yl]-1-ethyl-6,8-difluoro-1,4-dihydro-4-oxo-3-quinolinecarboxylic acid A mixture of 0.27 g (1 mmole) of 1-ethyl-6,7,8-trifluoro-1,4-dihydro-4-oxo-3-quinolinecarboxylic acid, 0.22 g (1.1 mmole) of 3-(exo-amino)-8-azabicyclo[3.2.1]octane dihydrochloride, 0.45 ml (3.0 mmole) of 1,8-diazabicyclo[5.4.0]undec-7-ene and 10 ml of acetonitrile was heated at reflux for 18 hours. After cooling to room temperature, a small amount of solid was removed by filtration and washed with ethanol. The combined filtrates were concentrated to 10 ml and refrigerated. The resulting solid was filtered, washed with ethanol and dried to give 0.14 g of the title compound, mp 220°–225° C.

EXAMPLE 22

7-[3-Endo-amino-8-azabicyclo(3.2.1)oct-8-yl]-1-ethyl-6-fluoro-1,4-dihydro-4-oxo-1,8-naphthyridine-3-carboxylic acid (a)

A solution of 0.81 g (3.0 mmol) of 7-chloro-1-ethyl-6-fluoro-1,4-dihydro-4-oxo-1,8-naphthyridine-3-carboxylic acid, 0.66 g (3.3 mmol) of 3-endo-amino-8-azabicyclo[3.2.1]octane dihydrochloride, 1.35 ml (9.0 mmol) of 1,8-diazabicyclo[5.4.0]undec-7-ene, and 30 ml of acetonitrile was heated under reflux for two hours and stirred at room temperature for three days. The solid was collected by filtration; dissolved with 35 ml of dilute ammonium hydroxide, filtered, and the solution was concentrated until the product precipitated. The title compound was filtered to give 0.40 g, mp 255°–259° C.

In a similar manner, the following compounds were prepared:

7-[3-Endo-amino-8-azabicyclo(3.2.1)oct-8-yl]-1-ethyl-6,8-difluoro-1,4-dihydro-4-oxo-3-quinolinecarboxylic acid (b), mp 208°–210° C., 7-[3-Endo-amino-8-azabicyclo(3.2.1)oct-8-yl]-1-cyclopropyl-6-fluoro-1,4-dihydro-4-oxo-1,8-naphthyridine-3-carboxylic acid (c), mp 238° C., and 7-[3-Exo-amino-8-azabicyclo(3.2.1)oct-8-yl]-1-cyclopropyl-6-fluoro-1,4-dihydro-4-oxo-1,8-naphthyridine-3-carboxylic acid (d), mp 215°–220° C.

EXAMPLE 23

7-[3-Exo(acetylamino)-8-azabicyclo[3.2.1]oct-8-yl]-1-ethyl-6-fluoro-1,4-dihydro-4-oxo-3-quinolinecarboxylic acid A mixture of 1.00 g (3.8 mmole) of 1-ethyl-6,7-difluoro-1,4-dihydro-4-oxo-3-quinolinecarboxylic acid, 0.8 g (3.8 mmole) of 3-exo(acetylamino)-8-azabicyclo[3.2.1] octane hydrochloride, 1.14 ml (7.6 mmole) of 1,8-diazabicyclo[5.4.0]undec-7-ene, and 50 ml of acetonitrile was heated under reflux for 18 hours. After cooling to room temperature, the reaction mixture was filtered and the solid was washed with acetonitrile and methanol to yield 0.55 g of the title compound, m.p.>300°.

EXAMPLE 24

7-[3-Exo(acetylamino)-8-azabicyclo[3.2.1]oct-8-yl]-1-ethyl-6-fluoro-1,4-dihydro-4-oxo-1,8-naphthyridine-3-carboxylic acid A mixture of 0.95 g (3.5 mmole) of 7-chloro-1-ethyl-6-fluoro-1,4-dihydro-4-oxo-1,8-naphthyridine, 0.72 g (3.5 mmole) of 3-exo(acetylamino)-8-azabicyclo[3.2.1]octane hydrochloride, 1.05 ml (7.0 mmole) of 1,8-diazabicyclo[5.4.0]undec-7-ene, and 30 ml of acetonitrile was heated under reflux for 2 hours. After cooling to room temperature, the reaction mixture was filtered and the solid was washed with acetonitrile and methanol to yield 0.99 g of the title compound, mp>300°.

EXAMPLE 25

7-[3-Endo(acetylamino)-8-azabicyclo[3.2.1]oct-8-yl]-1-ethyl-6-fluoro-1,4-dihydro-4-oxo-3-quinolinecarboxylic acid A mixture of 1.31 g (5.0 mmol) of 1-ethyl-6,7-difluoro-1,4-dihydro-4-oxo-3-quinolinecarboxylic acid, 1.23 g (6.0 mmol) of 3-endo(acetylamino)-8-azabicyclo[3.2.1]octane hydrochloride, 1.50 ml (10 mmol) of 1,8-diazabicyclo[5.4.0]undec-7-ene, 40 ml of acetonitrile and 10 ml of dimethyl formamide was heated under reflux for 19 hours. After cooling to room temperature, the reaction mixture was filtered and the solid was washed with acetonitrile and ethanol to give 1.04 g of the title compound, mp>300°.

EXAMPLE 26

7-[3-Endo(acetylamino)-8-azabicyclo[3.2.1]oct-8-yl]-1-ethyl-6-fluoro-1,4-dihydro-4-oxo-1,8-naphthyridine-3-carboxylic acid A mixture of 0.54 g (2.0 mmol) of 7-chloro-1-ethyl-6-fluoro-1,4-dihydro-4-oxo-1,8-napthyridine-3-carboxylic acid, 0.41 g (2.0 mmol) of 3-endo(acetylamino)-8-azabicyclo[3.2.1]octane, 0.6 ml (4.0 mmol) of 1,8-diazabicyclo[5.4.0]undec-7-ene, and 50 ml of acetonitrile was heated under reflux for 5 hours. After cooling to room temperature, the reaction mixture was filtered and the solid was washed with acetonitrile and water to give 0.37 g of the title compound, mp>300°.

EXAMPLE 27

7-[5-[(4-aminophenyl)methyl]2-,5-diazabicyclo[2.2.1]hept-2-yl]-1-cyclopropyl-6,8-difluoro-1,4-dihydo-4-oxo-3-quinolinecarboxylic acid A solution of 1.52 g (4.0 mmol) of 7-(2,5-diazabicyclo[2.2.1]hept-2-yl)-1-cyclopropyl-6,8-difluoro-1,5-dihydro-4-oxo-3-quinolinecarboxylic acid, 1.3 g (6.0 mmol) of 1-(bromomethyl)-4-nitrobenzene, 1.12 ml (8.0 mmol) of triethylamine and 40 ml of N-N-dimethylformamide was heated at 100° for 18 hours. The solution was evaporated to dryness and the residue was treated with water and filtered to give 1.61 g of 1-cyclopropyl-6,8-difluoro-1,4-dihydro-7-[5-[(4-nitrophenyl)methyl]-2,5-diazabicyclo[2.2.1]hept-2-yl]-4-oxo-3-quinolinecarboxylic acid, mp 177°–182°.

A solution of 1.33 g (2.54 mmol) of the above compound, 0.05 g 5% Pd/C and 100 1 of acetic acid was hydrogenated until the requisite amount of hydrogen uptake was observed. The reaction mixture was filtered and the filtrate was evaporated. The residue was dissolved with water and Na$_2$CO$_3$ solution was added to pH 7.0. The solid was collected by filtration to yield 0.37 g of the title compound.

EXAMPLE 28

In a similar manner to Example 27, 7-(2,5-diazabicyclo[2.2.2]oct-2-yl)-1-cyclopropyl-6-fluoro-1,4-dihydro-4-oxo-1,8-naphthyridine-3-carboxylic was alkylated with 1-(bromomethyl)-4-nitrobenzene and the product was hydrogenated to give 7-[5-[(4-aminophenyl)methyl]-2,5-diazabicyclo[2.2.2]oct-2-yl]-1-cyclopropyl-6-fluoro-1,4-dihydro-4-oxo-1,8-naphthyridine-3-carboxylic acid.

We claim:

1. A compound of the formula:

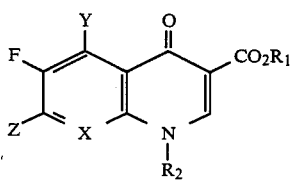

I wherein Z is

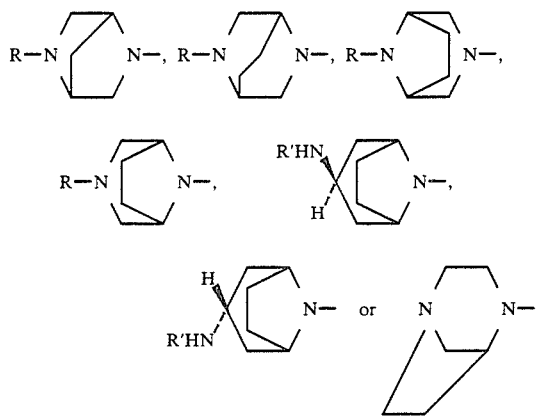

in which R is hydrogen, aklyl of one to three carbon atoms, hydroxyalkyl of two or three carbon atoms, benzyl, or p-amino-benzyl; $R^1$ is hydrogen or alkanoyl of from one to three carbon atoms; X is CH, CF, or N; Y is hydrogen, fluoro, or amino; $R_1$ is hydrogen, alkyl having from one to six carbon atoms or a cation; $R_2$ is alkyl having from one to four carbon atoms, vinyl haloalkyl, hydroxyalkyl having from two to four carbon atoms or cycloalkyl having three to six carbon atoms, or a pharamaceutically acceptable acid addition or base salt thereof.

2. A compound as claimed in claim 1, wherein Y is hydrogen.

3. A compound as claimed in claim 2, wherein $R_2$ is ethyl, vinyl, 2-fluoroethyl or cyclopropyl.

4. A compound as claimed in claim 3, wherein X is Cf, or N.

5. A compound as claimed in claim 4, wherein $R_1$ is hydrogen or a pharmaceutically acceptable base salt thereof.

6. A compound as claimed in claim 1 and being 7-(2,5-diazabicyclo[2.2.2]oct-2-yl)-1-ethyl-6,8-difluoro-1,4-dihydro-4-oxo-3-quinolinecarboxylic acid.

7. A compound as claimed in claim 1 and being 7-(2,5-diazabicyclo[2.2.2]oct-2-yl)-1-ethyl-6-fluoro-1,4-dihydro-4-oxo-1,8-naphthyridine-3-carboxylic acid.

8. A compound as claimed in claim 1 and being 7-(2,5-diazabicyclo[2.2.2]oct-2-yl)-1-cyclopropyl-6,8-difluoro-1,4-dihydro-4-oxo-3-quinolinecarboxylic acid.

9. A compound as claimed in claim 1 and being 7-(2,5-diazabicyclo[2.2.2]oct-2-yl)-1-cyclopropyl-6-fluoro-1,4-dihydro-4-oxo-1,8-naphthyridine-3-carboxylic acid.

10. A compound as claimed in claim 1 and being 7-[3-(exo-amino)-8-azabicyclo[3.2.1]oct-8-yl]-1-ethyl-6,8-difluoro-1,4-dihydro-4-oxo-3-quinolinecarboxylic acid.

11. A compound as claimed in claim 1 and being 7-[3-(exo-amino)-8-azabicyclo[3.2.1]oct-8-yl]-1-ethyl-6-fluoro-1,4-dihydro-4-oxo-1,8-naphthyridine-3-carboxylic acid.

12. A compound as claimed in claim 1 and being 7-[3-(exo-amino)-8-azabicyclo[3.2.1]oct-8-yl]-1-cyclopropyl-6,8-difluoro-1,4-dihydro-4-oxo-3-quinolinecarboxylic acid.

13. A compound as claimed in claim 1 and being 7-[3-(exo-amino)-8-azabicyclo[3.2.1]oct-8-yl]-1-cyclopropyl-6-fluoro-1,4-dihydro-4-oxo-1,8-naphthyridine-3-carboxylic acid.

14. A compound as claimed in claim 1 and being 7-(1,4-diazabicyclo[3.2.1]oct-4-yl)-1-ethyl-6,8-difluoro-1,4-dihydro-4-oxo-3-quinolinecarboxylic acid.

15. A compound as claimed in claim 1 and being 7-(1,4-diazabicyclo[3.2.1]oct-4-yl)-1-ethyl-6-fluoro-1,4-dihydro-4-oxo-1,8-naphthyridine-3-carboxylic acid.

16. A compound as claimed in claim 1 and being 7-(1,4-diazabicyclo[3.2.1]oct-4-yl)-1-cyclopropyl-6,8-difluoro-1,4-dihydro-4-oxo-3-quinolinecarboxylic acid.

17. A compound as claimed in claim 1 and being 7-(1,4-diazabicylo[3.2.1]oct-4-yl)-1-cyclopropyl-6-fluoro-1,4-dihydro-4-oxo-1,8-naphthyridine-3-carboxylic acid.

18. A compound as claimed in claim 1 being 1-cyclopropyl-6-fluoro-1,4-dihydro-7-(5-methyl-2,5-diazabicyclo[2.2.1]hept-2-yl)-4-oxo-1,8-naphthyridine-3-carboxylic acid.

19. A compound as claimed in claim 1 and being 1-cyclopropyl-6,8-difluoro-1,4-dihydro-7-(5-methyl-2,5-diazabicyclo[2.2.1]hept-2-yl)-4-oxo-3-quinolinecarboxylic acid.

20. A compound as claimed in claim 1 and being 7°-2,5-diazabicyclo(2.2.1)hept-2-yl]-1-ethyl-6,8-difluoro-1,4-dihydro-4-oxo-3-quinolinecarboxylic acid.

21. A compound as claimed in claim 1 and being 7-[2,5-diazabicyclo(2.2.1)hept-2-yl]-1-ethyl-6-fluoro-1,4-dihydro-4-oxo-1,8-naphthyridine-3-carboxylic acid.

22. A compound as claimed in claim 1 and being 1-cyclopropyl-7-[2,5-diazabicyclo(2.2.1)hept-2-yl]-6-fluoro-1,4-dihydro-4-oxo-1,8-naphthyridine-3-carboxylic acid.

23. A compound as claimed in claim 1 and being 1-cyclopropyl-7-[2,5-diazabicyclo(2.2.1)hept-2-yl]-6,8-difluoro-1,4-dihydro-4-oxo-3-quinolinecarboxylic acid.

24. A compound as claimed in claim 1 and being 1-ethyl-6-fluoro-7-(5-methyl-2,5-diazabicyclo-[2.2.2]oct-2-yl)-1,4-dihydro-4-oxo-1,8-naphthyridine 3-carboxylic acid.

25. A compound as claimed in claim 1 and being 1-ethyl 6,8-difluoro-7-(5-methyl-2,5-diazabicyclo-[2.2.1]hept-2-yl)-4-oxo-3-quinolinecarboxylic acid.

26. A compound as claimed in claim 1 and being 1-ethyl 7-(5-ethyl-2,5-diazabicyclo[2.2.1]hept-2-yl)-6,8-difluoro-1,4-dihydro-4-oxo-3-quinolinecarboxylic acid.

27. A compound as claimed in claim 1 and being 1-ethyl-7-[5-(1-methylethyl)-2,5-diazabicyclo-[2.2.1]hept-2-yl]-6,8-difluoro-1,4-dihydro-4-oxo-3-quinolinecarboxylic acid.

28. A compound as claimed in claim 1 and being 1-ethyl-6,8-difluoro-1,4-dihydro-7-[5-(2-hydroxyethyl)-2,5-diazabicyclo[2.2.1]hept-2-yl[-4-oxo-3-quinolinecarboxylic acid.

29. A compound as claimed in claim 1 and being 7-[5-(4-aminophenyl)methyl]-2,5-diazabicyclo-[2.2.2]oct-2-yl-1-cyclopropyl-6-fluoro-1,5-dihydro-4-oxo-1,8-naphthyridine-3-carboxylic acid.

30. A compound as claimed in claim 1 and being 7-[5-[(4-aminophenyl)methyl]-2,5-diazabicyclo-[2.2.1]hept-2-yl]-1-cyclopropyl-6,8-difluoro-1,4-dihydro-4-oxo-3-quinolinecarboxylic acid.

31. A pharmaceutical composition comprising an antibacterially effective amount of a compound as claimed in claim 1 together with a pharmaceutically acceptable carrier.

32. The method of treating bacterial infections in mammals which comprises administering to said mammal a pharmaceutical composition as claimed in claim 31.

* * * * *